United States Patent [19]
D'Alessio et al.

[11] Patent Number: 5,389,085
[45] Date of Patent: Feb. 14, 1995

[54] AUTOMATIC NEEDLE PROTECTOR

[75] Inventors: Larry M. D'Alessio, Manasquan, N.J.; John F. Romano, Washington Crossing, Pa.

[73] Assignee: International Medical Consultants, Inc., Washington Crossing, Pa.

[21] Appl. No.: 159,053

[22] Filed: Nov. 29, 1993

Related U.S. Application Data

[63] Continuation-in-part of Ser. No. 16,285, Feb. 11, 1993, Pat. No. 5,292,314.

[51] Int. Cl.[6] .............................................. A61M 5/32
[52] U.S. Cl. .................................................... 604/198
[58] Field of Search ............................... 604/192–198, 604/263, 110

[56] References Cited

U.S. PATENT DOCUMENTS

| 4,723,943 | 2/1988 | Spencer | 604/198 |
|---|---|---|---|
| 4,801,295 | 1/1989 | Spencer | 604/198 |
| 4,894,055 | 1/1990 | Sudnak | 604/198 |
| 4,911,693 | 3/1990 | Paris | 604/198 |
| 4,923,447 | 5/1990 | Morgan | 604/198 |
| 4,932,940 | 6/1990 | Walker et al. | 604/198 |
| 5,049,136 | 9/1991 | Johnson | 604/198 |
| 5,092,851 | 3/1992 | Ragner | 604/192 |
| 5,104,384 | 4/1992 | Parry | 604/198 |
| 5,122,123 | 6/1992 | Vaillancourt | 604/192 |
| 5,169,392 | 12/1992 | Ranford et al. | 604/198 |
| 5,195,983 | 3/1993 | Boese | 604/192 |
| 5,201,708 | 4/1993 | Martin | 604/110 |
| 5,279,583 | 1/1994 | Shober, Jr. et al. | 604/198 |

Primary Examiner—C. Fred Rosenbaum
Assistant Examiner—Frank Wilkens, III
Attorney, Agent, or Firm—Weingarten, Schurgin, Gagnebin & Hayes

[57] ABSTRACT

A syringe has a needle mounted in the lower end of a tubular mount. A protective cover, in the form of a sleeve, fits over this lower end of the tubular mount, and extends to fully cover the sharp end of the needle. The tubular mount has a pair of elongated, axial slots for the entry and exit of a cog or lug on the inside of the sleeve. Pressure on the sleeve slides the lug up the entry slot and exposes the needle. A cross over slot carries the lug to the exit slot, where it slides down to the lower end of the mount, and over a locking ridge to automatically and securely recover the needle. A spring, coupled between the mount and the sleeve has an axial force urging the sleeve down in either slot, and a rotary force urging the cog towards the exit slot. The lug must be in the entry slot to depress and use the needle, but the lug is then rotated to the exit slot and returned by the spring, automatically, to lock the lug in the safe, covering position of the sleeve. In a further embodiment, a mount is provided having a needle supporting hub attached to an upper end, an open lower end, and an aperture in the side of the mount. A protective cover fits inside of the mount and has a protruding lug which engages the mount aperture. A spring coupled between the mount and the cover is subjected to rotational and compressive forces to automatically urge the cover to the needle protection position.

28 Claims, 4 Drawing Sheets

AUTOMATIC NEEDLE PROTECTOR

RELATED CASE INFORMATION

This application is a continuation-in-part application of application Ser. No. 08/016,285, filed Feb. 11, 1993, U.S. Pat. No. 5,292,31.

BACKGROUND OF THE INVENTION

The use of needles for penetrating the body is essential in modern medicine. Their uses include injecting fluids into, or drawing blood or other fluids out of almost any part of the body. The sizes of the needles, and the associated syringe equipment, will vary according to their function.

However, regardless of the size, use, or function, the needle is inevitably a sharp and potentially hazardous object. It should be safely stored, and, more important, safely discarded after any use. This is mandatory at all health facilities, but the facts prove that, with human nature, and overworked, human hospital staffs, used needles will always be found, and will always be a potential hazard.

The potential danger in needles is, of course, in used needles that may have picked up a virus of some kind from anyone using, or being injected by a needle. Once used, the needle must be considered contaminated, and, even if the risk is microscopic, it is a potential threat to the next person who, accidentally or otherwise, comes in contact with the needle. With certain deadly viruses living in a few human beings today, no gamble, however microscopic, is tolerable.

All hospitals, and other users of needles, have established systems and rules for the control of the use of and disposition of needles. Most of these are almost foolproof, and restrict the use of needles to well trained professional personnel. However, it is now these, valuable people who are at risk from the casual, unprotected needle that may have been accidentally overlooked, and just lying around. Contact with this needle could be equally unpredictable. One could be standing, sitting, or in motion of any kind, and the contact could be with any part of the body.

Again, the risk of a trained medical technician coming in contact with a stray needle—let alone its sharp end—should be negligible, and, that this particular needle might be infected, would be another very-remote possibility, but, where that possibility, however remote, could be lethal, or harmful in any way, the stakes are still too high.

The obvious, and basic, solution to the problem would be to have a safety shield or cover over the needle, before and after it is used. This is done quite effectively in several of the systems, but, in most of the systems, it relies on the human function of putting on, taking off, and putting the safety shield back on before discarding the needle in the required manner.

What is needed is a safety shield that is part of the needle structure, and that is locked in a position that covers and protects the sharp end of the needle. There must be a means for uncovering the safety shield, and activating the device for use, at least one time, but the safety shield must be returned, automatically, to its locked, protective position immediately after use.

SUMMARY OF THE INVENTION

A surgical needle projects from the lower end of a tubular structure. A protective cover, or shield, in the form of a tubular sleeve, slightly larger than the tubular structure, has an upper end fitting over the lower end of the tubular structure. The lower end of the sleeve must completely cover and guard the sharp end of the needle. Elongated, generally axial, entrance and exit slots are formed in the tubular structure, between its lower and upper ends to engage a spring-loaded lug on the underside of the tubular sleeve. This allows the sleeve to move upward, with the lug sliding along the entrance slot of the tubular structure, to uncover the needle. The lug then rotates through a change-over slot, to the exit slot, to be forced downward and lock at the base of the exit slot, to recover and guard the needle. A spring connected between the tubular structure and the sleeve provides a radial torque to urge the lug from the entrance slot, through a change-over slot, toward the exit slot. The spring also provides an axial force to oppose the uncovering of the needle and to urge the sleeve, always, toward its needle-covering and locking position. The upper end of the tubular structure will be provided with a luer, or other fitting to couple the needle assembly to its intended function.

In accordance with the further embodiment of the invention, a tubular mount is provided with a hub attached to an upper end, an open lower end, and an aperture in a side of the mount. The hub has a needle extending from a lower end and a fitting at an upper end for coupling to a barrel and plunger assembly. A protective cover is provided having a diameter smaller than that of the mount so that an upper end of the cover fits inside of the lower end of the mount. The cover has an apertured lower end and is adapted for being in a needle protection position in which the tip of the needle is covered by the cover or a retracted position in which the needle extends through the apertured lower end of the cover to be exposed for use. A lug protrudes from a tab on the cover to engage the aperture in the side of the mount so that, as the cover is moved between the needle protection position and a retracted position, the lug moves in the aperture toward the upper end of the mount. The aperture includes an entrance position adjacent to the lower end of the mount and an armed position radially spaced from the entrance position by an angled portion of the mount. The needle protector is armed by rotating the cover to move the lug from the entrance position along the angled portion and to the armed position. A spring is coupled between the mount and the cover so that when the device is armed, a rotary torque is imparted to the spring. Movement of the cover to a retracted position upon actuation of the device causes the spring to be subjected to a compressive force. The torsional and compressive forces on the spring cause the lug to be urged back to the entrance position, thereby automatically causing the cover to return to the needle protection position.

DETAILED DESCRIPTION OF THE INVENTION

Figure 1:
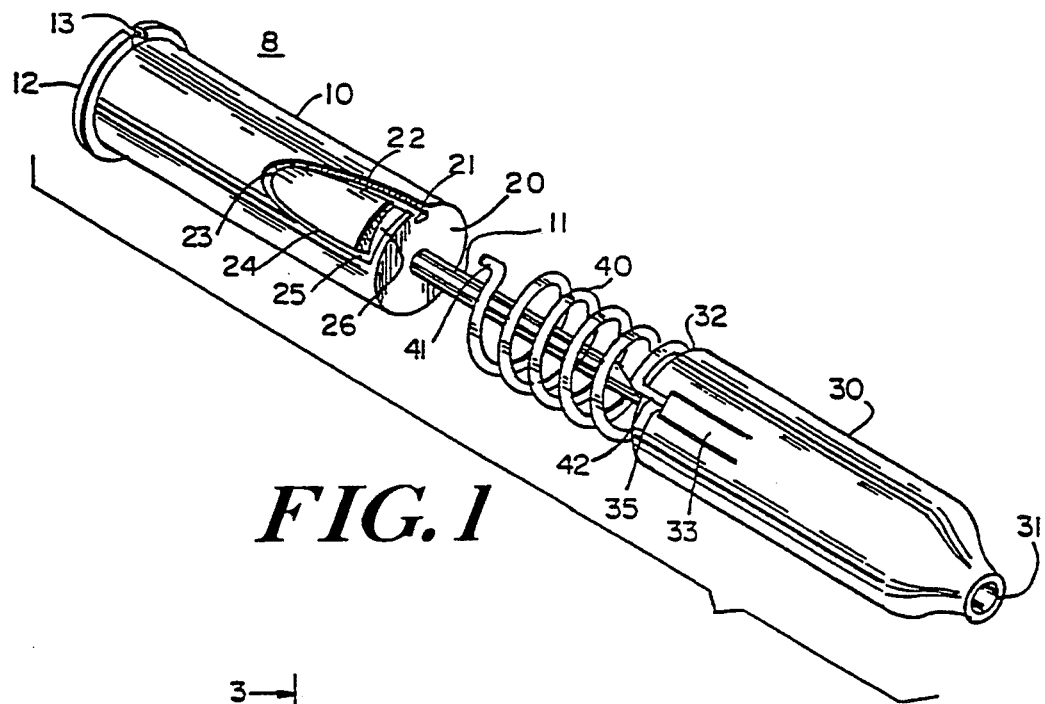
FIG. 1 shows an isometric, exploded view of the device.

Referring now more particularly to FIG. 1, and isometric view of the basic device 8 is shown in an exploded form to clearly illustrate the elements that interact to provide the automatic, safety, needle protector. An upper portion 10 is a hollow tubular mount that supports a needle 11 at one, lower end 20. The other, upper end has a flange 12, with a notch or slot 13 to accommodate the upper end 41 of a spring 40 in a manner that will be described later.

Figure 3:
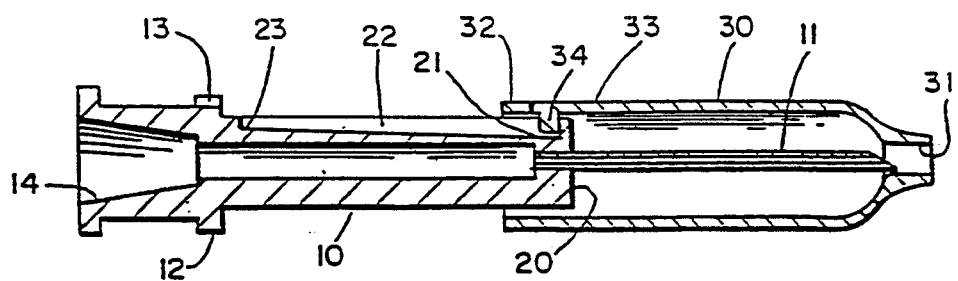
FIG. 3 shows a cross section of the device along the lines 3—3 of FIG. 2.

This other, upper end of the tubular sleeve 10 will, normally, include one of the conventional couplings for a syringe, such as the luer fitting 14 shown in FIG. 3. This has been omitted here, and in the other drawings, for simplicity. Other fittings for similar functions can also be accommodated.

The needle 11 is mounted in the center of the base 20 at the lower end of the tubular needle mount 10, in a well known manner. The sharp point, or tip, of the needle will be protected by a cover or sleeve 30.

This exploded view shows, quite clearly, typical slots in the needle mount that control the position and function of the protective cover 30 for the needle in a manner that will be illustrated in the other figures and described in more detail in due course.

These typical slots include an opening 21 for an elongated starting or entrance slot 22 that goes up to a change-over slot 23, that leads to an elongated exit slot 24 that ends in a locking ledge 25 that automatically locks the protective cover 30, with its lower end 31 over the needle.

The protective cover 30 has an opening 31 in its lower end that the needle can extend through when its inner lug 34 is moving through the slots 22, 23, and 24, and the device is in use. The other, upper end 32, as noted earlier, is open and forms the sleeve that fits loosely around the tubular needle mount 10. A notch 35 may be provided in the upper end 32 of the sleeve 30 to support the lower end 42 of the spring 40, as shown. This spring 40 provides the automatic operation of the protective cover.

Figure 4A:
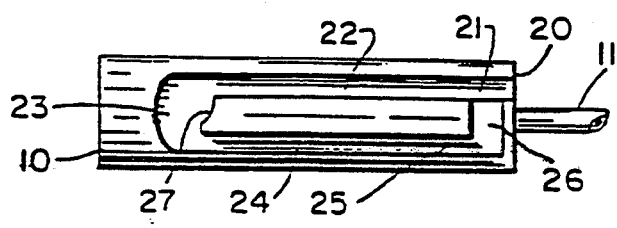
FIG. 4A shows a top view of the needle mount normal to the lines 4—4 of FIG. 2.
Figure 4:
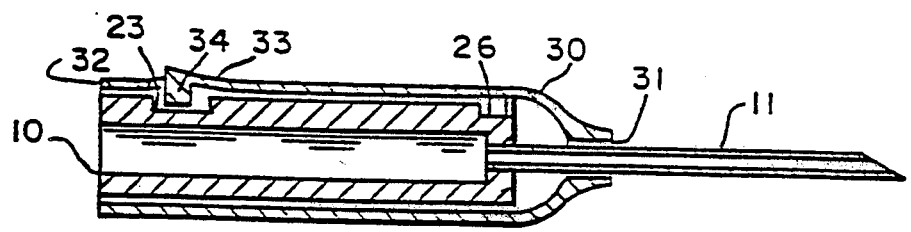
FIG. 4 shows a cross section of the device along the lines 4—4 of FIG. 2.
Figure 5:
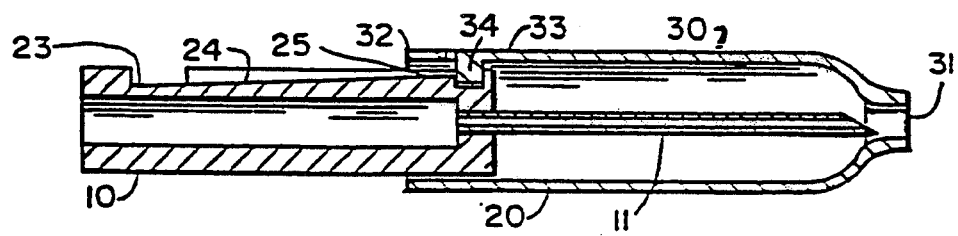
FIG. 5 shows a cross section of the device along the lines 5—5 of FIG. 2.

Another, flat spring 33 actuates a lug or cam 34, seen in FIGS. 3, 4, and 5, that rides in the slots 21 through 26 for the automatic control of the protective sleeve.

The spring 40 would, in operation, fit loosely over the tubular needle mount 10. The upper end clip 41 would fit into, and may be secured in the notch or slot 13 of the flange 12. The lower end clip 42 would fit into the notch or slot 35, as noted earlier, and may also be secured therein.

Figure 2:
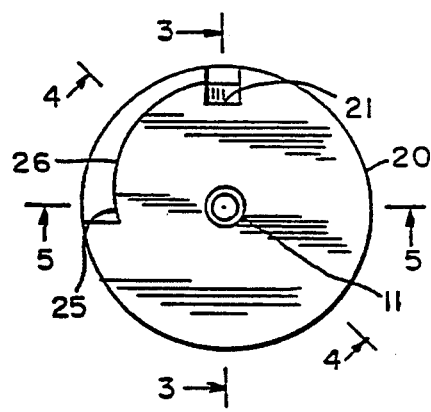
FIG. 2 shows a plan view of the needle mount.

FIG. 2 shows a plan view of the lower end 20 of the tubular needle mount, seen along the needle 11. This, more clearly, shows the opening 21 for the start of the lug 34, mounted on the underside of the spring 33, through its automatic locking path. This also shows the ledge 25, at the end of the slot 24, that secures the lug or cog 34 and locks the protective cover 30, with its end 31 well over the sharp end of the needle. Actually, the needle can be reactivated by rotating the sleeve 30, and moving its cog up the ramp 26 to drop back into the starting slot at 21.

FIG. 3 shows a cross section of the device along the lines 3—3 of FIG. 2. This shows the protective sleeve 30 with its upper end 32 over the tubular mount 10, its lower end 31 covering and protecting the sharp end of the needle 11, and its cog 34 started in the opening 21. The slot 22 will guide the cog to the change-over slot 23, and may raise it partially in the process. This figure also shows the flange 12, with the notch or slot 13 to accommodate the upper, outer end clip 41 of the spring 40.

The spring 40 is not shown in this and the subsequent drawings for simplicity and clarity in illustrating the other, most important elements of the safety cover, and their complex functions.

A typical luer fitting 14 is illustrated in this figure. Obviously this-or a similar coupling-would be necessary for coupling this safety device to any conventional unit that needs a hypodermic needle, which is the normal function of this device.

FIG. 4 shows another cross section of this device along the lines 4—4 of FIG. 2. This shows the protective sleeve or cover 30 drawn to the upper end of the tubular mount 10. This shows the cog 34, on the flat spring 33 of the sleeve 30 in the cross-over slot 23, and the needle fully exposed. As in all of these figures, similar elements are similarly numbered. The luer fitting 14 is, again, omitted for simplicity in this and the rest of these drawings.

FIG. 4A is a top view of the tubular mount 10 for mounting the needle 11, normal to the lines 4—4 of FIG. 2, and is added to illustrate another variation of the slots 21 through 26. This is the version that is, actually, used in the drawings 3, 4, and 5. To this has been added a notch 27 along the cross-over 23. This would hold the lug 34 against the pressures of the spring and would allow the protective cover 30 to be held with the needle exposed, if necessary, while it is being inserted or used. Subsequent movement or use of the cover 30 would complete the cycle, along the path of the lug 34, to the slot 24 and to the ledge 25, to lock the protective cover 30 in its safe position.

This figure also shows more depth to the cross-over 23. Actually this cross-over could extend from near the top of the slots to near the lower end of the mount. This could provide the essential, automatic safety locking of the sleeve with a minimal penetration of the needle, which might be advisable in many cases.

FIG. 5 is another cross section of the device, along the lines 5—5 of FIG. 2, and this shows the protective cover at the end of its cycle, with the lug 34 of the protective cover system locked against the ledge 25, and the end of the cover 31 well over the tip of the needle 11.

This shows the cross-over slot 23 and the slot 24 with its ramp that carries the cog 34 up until it passes over the ledge 25, where the pressure of the spring 33 depresses the lug 34 to lock the safety shield in its safe condition. The spring 40, of course, in its axial pressure urges the cover and lug along the slot 24 to the locking position.

Figure 6:
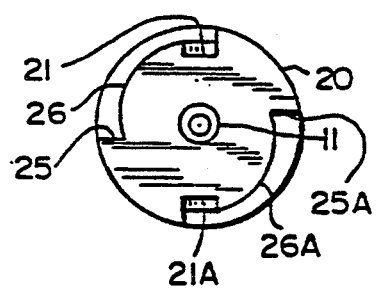
FIG. 6 shows a plan view of another variation of the needle mount.

FIG. 6 is another plan view of the bottom 20 with a variation of the needle holder, again in line with the needle 11. This shows an additional slot 21A, a ledge 25A, and a resetting slope 26A to accommodate an additional lug, not shown, to double the strength and the safety of the automatic locking function. Additional combinations of slots and lugs could, obviously, be added for additional strength and safety.

In operation, the device would normally be assembled with the elements of FIG. 1 compressed to the profile of FIG. 3. For example, the spring 40 would fit loosely over the tubular needle mount 10, with its upper end 41 seated in the notch 13 of the mount. This holds the protective cover, or sleeve 30 with its outer end 31 covering the sharp end of the needle 11, and its inner end fitting over the lower end 20 of the tubular needle mount. The lower end of the spring 42 is secured into the slot 35 of the protective cover, to hold the cog 34, mounted in the cover, in line with and against the ledge 25 so that the protective cover cannot be pushed back to expose the sharp end of the needle, whether it has been used or not.

When it is time to use the needle, for any reason, the needle mount 10 can be coupled to an appropriate syringe, or other device at its fitting 14. The cover or sleeve 30 can then be rotated—in this case clockwise—to move the cam 34 up the slope 26 to drop into the opening 21 at the start of the slot 22. This puts a rotary torque on the spring 40 which urges the cam back to the angle of the slot 24, which leads back to its locking ledge 25. However, the only way the cam can get back from its starting position 21 is to slide along the slots 22, 23, and 24 to be lifted and dropped back into the locking position at 25.

In other words, once the protective cover or sleeve is armed or cocked, the spring exerts a rotary pressure on the cover to urge the cam back towards its exit slot 24, and its locking position at 25. The spring also exerts an axial pressure on the cover to hold it in position over the sharp end of the needle until it is being used. The spring is then compressed axially to expose the needle for use, while moving the cam along the slots 22 and 23. Then the cam can only follow the slot 24 to return the cam, automatically, by the combined rotary and axial pressures of the spring, to its safe, locking position over the ledge 25, where the sharp end of the now used needle is automatically and permanently protected against accidental penetration of anything or anybody.

The spring, here, has this double function, and insures the automatic operation of the safety protective cover. The spring may be made of any springy material, from metal to plastic, and may be of any suitable, functional shape. Actually, the spring 40 may be molded as part of the sleeve 30, when suitable materials are chosen.

The materials chosen would presumably be of plastic. Both the protective cover, with or without the spring, and the tubular mount for the needle would, obviously, be molded for mass production and cost effectiveness. While the safety of medical workers is of prime importance, the cost of providing safety should be reasonable.

The object of this invention is to provide the best possible, and almost fool-proof protection, at a minimal cost.

It should be noted that these units are disposable—as must all needle mounts be—but these are permanently protected wherever they are disposed. The law, of course, meticulously requires a very special disposal of all medical wastes, which means there is no problem. However, sadly, human error, indifference, or duplicity loads our beaches and other facilities with medical wastes.

The mount 10 that physically supports the needle, which is the essential element of this device, is standard, and similar to many standard needle holders, that couple a needle to a luer, or other fitting, for its ultimate use. However, this unit may be slightly longer to accommodate the motion of the protective sleeve over the needle and mount.

The length of the sleeve, and the mount, will vary with the length and size of the needle, which will vary according to its many uses. The size and shape of the device will vary, along with the ultimate use. This will, again, be a function of the size, and length of the needle. The smallest possible would, of course, be most desirable.

A solid, thin cap over the base 20, at the lower end of the mount would be very easy to attach, and desirable for locking the lug in both directions. This would prevent the sleeve from being pulled off the needle mount, as well as from being pushed in to expose the needle, which would virtually eliminate exposure of the needle in any manner. In this case, a secondary means for raising the spring 33 would be needed to fit the lug 34 in either the starting slot or the locking ledge.

This could also avoid the need for, or use of the slope 26, which could be eliminated, to avoid the accidental rotation of the sleeve to arm the device.

The protective sleeve 30, as well as most of the rest of the device, would be of plastic for ease of manufacture. The sleeve should be as small as practical, and quite transparent to allow the needle to be seen and controlled. The opening at 31 may be the full size of the sleeve, or may be just large enough, as shown, for the needle to fit through.

Figure 7:
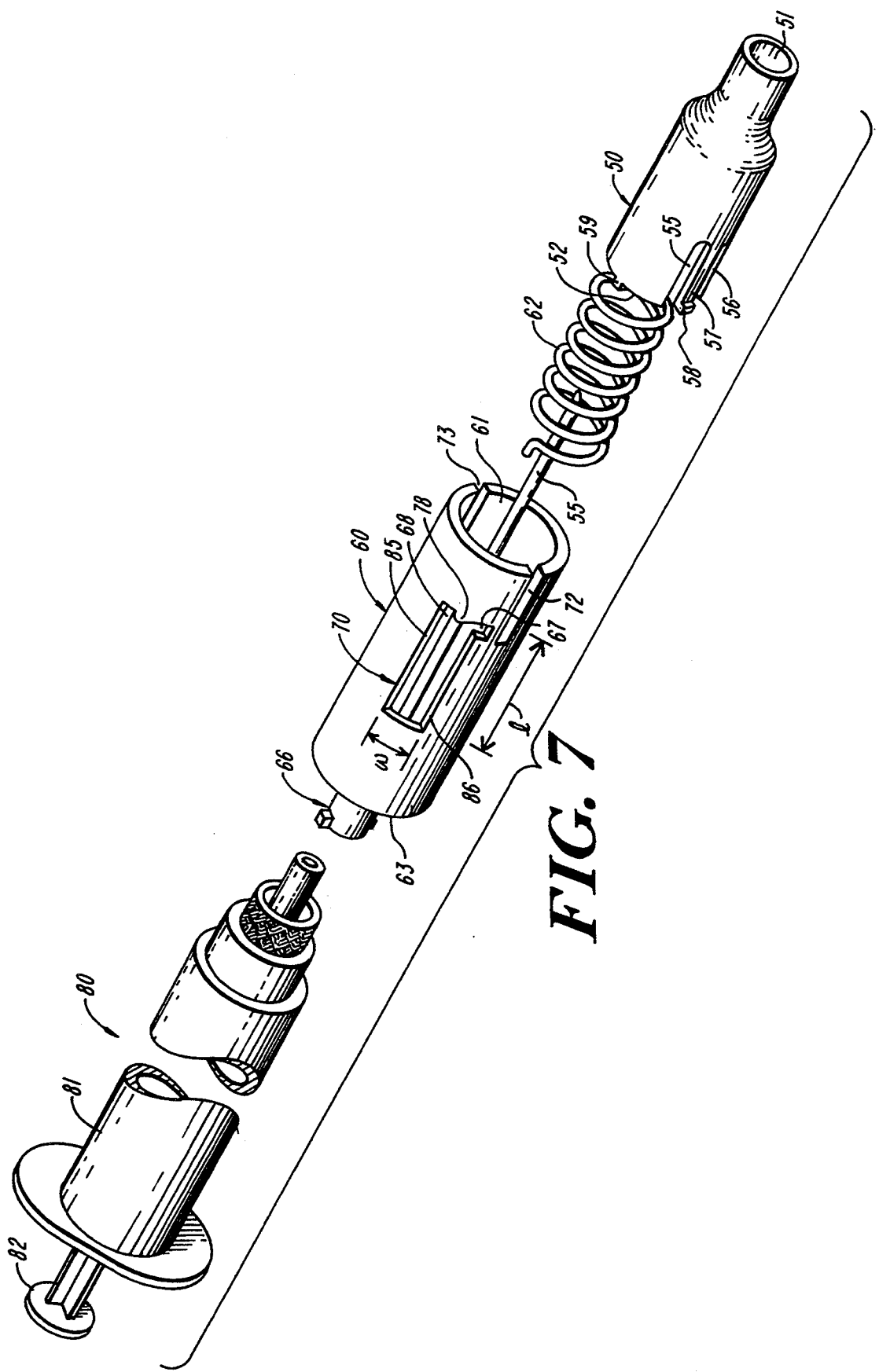
FIG. 7 shows an isometric, exploded view of a further embodiment of the invention with an exemplary barrel and plunger assembly.
Figure 8:
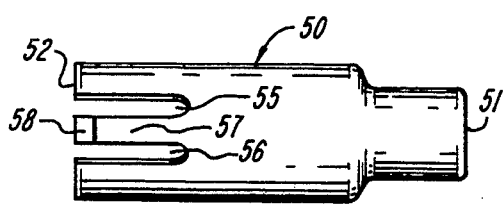
FIG. 8 shows a side view of the protective cover of the device of FIG. 7.

Referring to FIG. 7, a further embodiment of the invention is shown to include a protective cover, or sleeve 50 which fits inside a hollow, tubular mount 60. The protective cover 50 has an opening 51 at its lower end of a diameter suitable for permitting a needle 55 to extend therethrough during use. The diameter of the upper end 52 of the cover 50 is smaller than that of the mount 60 into which the cover extends. The protective cover 50 includes a pair of notches 55, 56 at the upper end 52 which are spaced to provide a cantilevered tab 57 therebetween. An upper end of the tab 57 has a lug 58 protruding therefrom, as shown also in FIG. 8. The cantilevered arrangement of tab 57 provides the tab with a resiliency which is advantageous during assembly of the device, as will be described.

Figure 9:
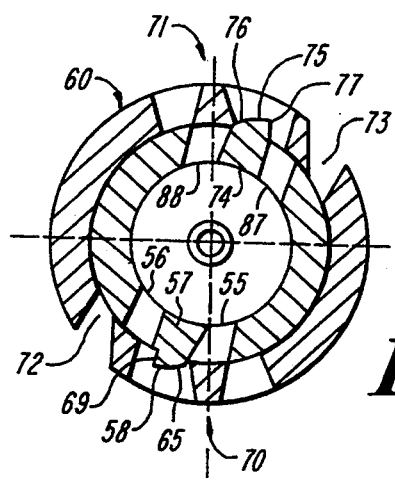
FIG. 9 shows a cross sectional view of the assembled device of FIG. 7.

Referring also to FIG. 9, a second, like tab 74 and a second pair of notches 87, 88 are provided in the upper end of the cover 50 at opposing locations with respect to the tab 57 and notches 55, 56, respectively. The second tab 74 has a lug 75 protruding therefrom, like lug 58. Each of the lugs 58, 75 has a tapered edge 65, 76, respectively, which further facilitate assembly of the device, and a flat edge 69, 77, as shown.

A spring 62 provides automatic operation of the protective cover 50 in response to axial and torsional forces applied during operation, as will be described. Suffice it here to say that the spring 62 is coupled between the protective cover 50 and the mount 60 with a lower end of the spring 62 attached to the cover 50 and an upper end attached to the mount 60. Specifically, the lower end of the spring has a hook portion which extends through a loop 59 on the upper end 52 of the cover 50.

The hollow, tubular mount 60 has an open lower end 61 for receiving the upper end 52 of the protective cover 50 and an upper end 63 coupled to a hub 66. More particularly, the upper end 63 of the mount 60 has an opening for receiving the hub 66, as can be seen in the cross-sectional views of FIGS. 11 and 12. The hub 66 supports the needle 55 at a lower end and has a coupling, or fitting, such as a luer fitting, at an upper end for mating with a conventional syringe barrel and plunger assembly. One exemplary assembly 80 is shown in FIG. 7 to include a barrel 81 and plunger 82. Various means for fastening the hub 66 to the mount 60 are suitable, such as sonic welding. Both the barrel and plunger assembly 80, as well as the hub and needle assembly 66 may be conventional, commercially available assemblies. The spring 62 is secured to the upper end of the mount 60 by locating the upper end of the spring 62 in a hole 64 in the upper end 63 of the mount 60 (see FIGS. 11 and 12).

Referring also to FIG. 9, the tubular mount 60 has two apertures 70, 71 and a pair of slots 72, 73, each one corresponding to one of the apertures 70, 71, respectively, and being spaced therefrom. Slots 72, 73 facilitate assembly of the device, as will be described. Each of apertures 70, 71 has a width labelled "w", a length labelled "1", and permits the protective cover 50 to be in a needle protection position, an armed position, or in one of a plurality of retracted positions during use of the device when the needle 55 is exposed.

Considering exemplary aperture 70 and slot 72, the lug 58 engages the aperture 70 and is moveable within the constraints of the aperture 70 to provide the cover 50 in the needle protection position, the armed position, or a retracted position. That is, the lug 58 protrudes through the aperture 70, slightly beyond the inner diameter of the mount 60, so that the edges, or walls of the aperture 70 restrict the movement of the lug 58 and cover 50. However, preferably, the lug 58 does not protrude beyond the outer diameter of the mount 60 in order to prevent potential undesirable interference with actuation of the device.

The needle protection position of the cover 50 corresponds to the lug 58 being located in a first, entrance position 67 of the aperture 70. The armed position corresponds to the lug 58 being in a second, armed position 68 of the aperture 70. When the cover 50 is in a retracted position, the lug 58 is located above the entrance and armed positions 67, 68 and toward the upper end of the mount 60 between an entrance wall 85 and an exit wall 86 of the aperture 70. The entrance and armed positions 67, 68 of the mount aperture 70 are radially spaced by an angled portion 78 of the mount 60. While the operation of the device is described with respect to exemplary lug 58 and aperture 70, it is understood that aperture 71 has like features for engaging corresponding lug 74.

The mount 60 and the protective cover 50 may be comprised of any material having suitable strength and other desired characteristics, such as plastic. Additionally, the mount 60 and cover 50 may be manufactured by any conventional technique, such as injection molding. Preferably, the cover 50, and at least the lower end 51 thereof, is made from a transparent material so that the tip of the needle 55 is visible in order to facilitate proper insertion into a needle receiving surface, such as a patient's arm. Spring 62 may be made of any suitable material providing a spring characteristic, such as metal or plastic. It should be understood that the selected materials and method of manufacturing the components of the device will vary in accordance with, inter alia, application requirements and cost considerations.

In assembling the device, mount 60 is fastened to the hub 66 as noted above, such as by a sonic welding process. The upper end of the spring 62 is positioned in the hole 64 at the upper end 63 of the mount 60 and the lower end of the spring 62 is attached to the cover 50 and specifically, to the loop 59. With the spring 62 thus coupled between the mount 60 and the cover 50, the cover 50 is guided into the larger diameter mount 60 with tabs 57, 74 aligned with corresponding slots 72, 73. Once the cover 50 cannot be inserted further into the mount 60 (i.e., once lugs 58, 75 contact the upper ends of the slots 72, 73), the cover 50 is rotated clockwise. Upon such rotation of the cover 50, the cantilevered tabs 57, 74 are deflected slightly inward toward the inside of the mount 60. This rotation of the cover 50 is facilitated by the tapered edges 65, 76 of the lugs 58, 75, respectively.

Figure 10:
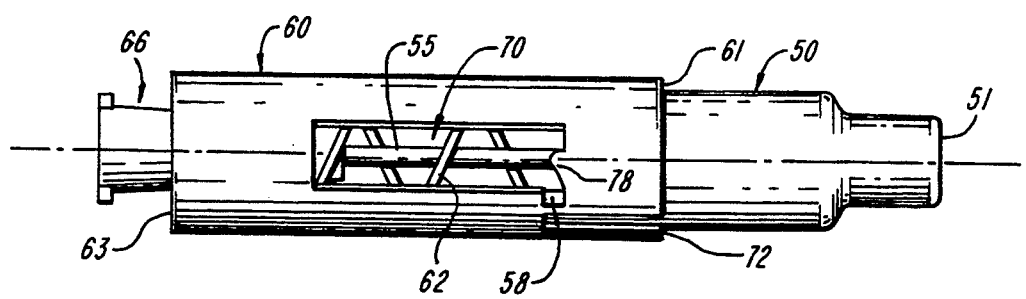
FIG. 10 shows a side view of the assembled device of figure 7.

Considering exemplary slot 72, aperture 70, and lug 58, once the lug 58 enters the entrance position 67 of aperture 70, the cover 50 is prevented from rotating counterclockwise due to the flat edge 69 of the lug 58 contacting the side of the entrance position 67 of the mount 60 adjacent to the slot 72. The assembled device is shown in FIG. 10 with the lug 58 positioned in the entrance position 67 of the aperture 70. In this position, the protective cover 50 extends over the tip of the needle 55 and cannot be pushed straight back to expose the needle 55 since the back wall of the entrance position 67 prevents such movement of the lug 58. With the cover 50 disposed in this needle protection position, the spring 62 is in a partially compressed state. Additionally, the spring 62 is subjected to a slight rotary torque, or torsional force, as a result of the rotation of the spring 62 as the cover 50 was rotated to move the lug 58 from the slot 72 to the entrance position 67.

When use of the needle 55 is desired, the hub 66 is coupled to a conventional syringe barrel and plunger assembly, such as the exemplary assembly 80 shown in FIG. 7. The upper end of the hub 66 has a fitting, such as a luer fitting, for this purpose. Thereafter, the device may be armed, or cocked, in preparation for use by rotating the cover 50 clockwise which causes the lug 58 to move along the angled portion 78 of the mount 60 that separates the entrance position 67 from the armed position 68. As the lug 58 clears the angled portion 78, an audible click occurs, indicating to the user that the device is armed and ready for use. By moving the lug 58 to the armed position, an additional rotary torque is exerted on the spring 62 which, upon actuation of the device, urges the lug 58 back to the entrance position 67.

Figure 11:
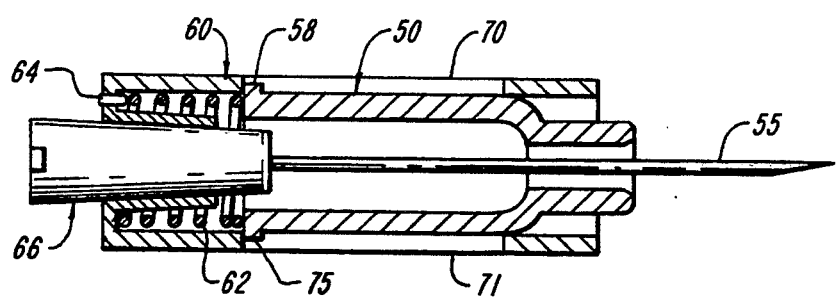
FIG. 11 shows a cross sectional view of the assembled device of FIG. 7 with the protective cover in a retracted position.
Figure 12:
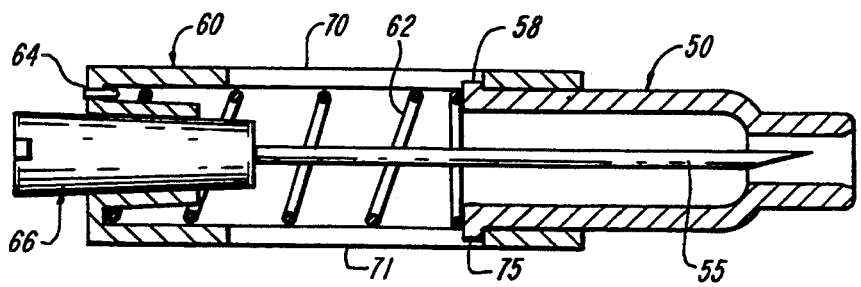
FIG. 12 is a cross sectional view of the assembled device of FIG. 7 with the protective cover in a needle protection position.

As the lower end of the cover 50 is pushed against a needle receiving surface, the cover 50 is forced further inside the mount 60, as shown in the view of FIG. 11. Such actuation of the device causes the spring 62 to be subjected to an additional axial, compressive force, as is apparent from the view of FIG. 11, and causes the lug 58 to move from the armed position 68 along the entrance wall 85 of the slot 70 and toward the upper end of 63 of the mount 60.

The torsional and compressive forces exerted on the spring 62 urge the protective cover 50 back to the needle protection position in which the lug 58 is located in the entrance position 67. Thus, upon removal of the needle 55 from the receiving surface, the protective cover 50 automatically moves to the needle protection position in which the needle tip is covered. Specifically, the rotary torque on the spring 62 causes the cover 50 to move radially, rotating counterclockwise so that the lug 58 contacts the exit wall 86 and the compressive force on the spring 62 causes the cover 50 to move outward from the mount 60 to the needle protection position shown in FIGS. 10 and 12. It is noted that once the lug 58 has returned to the entrance position 67, the device may be reactivated by re-arming the device for further use. That is, once the lug 58 has returned to the entrance position 67, the device can be re-armed by rotating the cover 50 clockwise which causes the lug 58 to move along the angled portion 78 of the mount 60 separating the entrance position 67 and the armed position 68, in the manner described above.

In view of the above described operation of the device, it should be understood that the dimensions of the apertures 70, 71 may be varied in accordance with a particular application. For example, a longer needle 55 may require that the aperture 70 have a greater length "1" to permit a desired exposure of the needle 55. Additionally other device dimensions, such as those of the mount 60 and the cover 50, may be readily varied as required in a particular application.

While the embodiment of FIGS. 7-12 is shown to have two opposingly disposed tabs 57, 74, apertures 70, 71, and slots 72, 73, it should be appreciated that a single tab, aperture, and slot arrangement may be suitable in certain applications.

The needle protector arrangements described herein are useable with conventional syringe barrel/plunger assemblies, such as the exemplary assembly 80 of FIG. 7, so that inventory of such assemblies need not be discarded and replaced in order to use the described devices. Additionally, by modifying the mount 10 to provide slots 22-26 (FIGS. 1-6) and the mount 60 to provide apertures 70, 71 (FIGS. 7-12), the advantages of the present needle protector embodiments are achieved without requiring additional parts.

Having described the preferred embodiments of the invention, it will be apparent to one of skill in the art that other embodiment incorporating their concepts may be used. Accordingly, the invention should be limited only by the spirit and scope of the appended claims.

We Claim:

1. A needle protector device comprising:
a needle having a tip;
a hub having an upper end adapted for coupling to a unit operative with said needle and a lower end to which said needle is attached;
a mount having an upper end coupled to said hub, an open lower end, and an aperture disposed in a side thereof, said aperture including an entrance position and an armed position radially spaced from said entrance position by a portion of said mount protruding into said aperture; and
a protective cover having a diameter smaller than the diameter of said mount, said protective cover having an upper end disposed inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture, wherein said device is armed by rotating said cover to move said lug from said entrance position over said protruding portion of said mount and to said armed position.

2. A needle protector device comprising:
a needle having a tip;
a hub having an upper end adapted for coupling to a unit operative with said needle and a lower end to which said needle is attached;
a mount having an Upper end attached to said hub, an open lower end, and an aperture disposed in a side thereof;
a protective cover having a diameter smaller than the diameter of said mount, said protective cover having an upper end fitting inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture; and
a spring coupled between said mount and said protective cover for providing an axial force and a torsional force to move said protective cover from said retracted position to said needle protection position.

3. A needle protector device comprising:
a needle having a tip;
a hub having an upper end adapted for coupling to a unit operative with said needle and a lower end to which said needle is attached;
a mount having an upper end attached to said hub, an open lower end, and an aperture disposed in a side thereof; and
a protective cover having a diameter smaller than the diameter of said mount, said protective cover having an upper end fitting inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture, wherein said aperture includes an entrance position adjacent to said lower end of said mount and an armed position radially spaced from said entrance position by an angled portion of said mount, wherein said device is armed by rotating said cover to move said lug from said entrance position to said armed position, and wherein said mount has an assembly slot extending from said lower end of said mount toward said upper end of said mount through which said lug is directed during assembly.

4. The needle protector device recited in claim 3 wherein said cover has a cantilevered tab disposed at said upper end of said cover and supporting said lug, said lug having a tapered edge which contacts said mount when said lug is moved from said assembly slot to said entrance position of said aperture during assembly causing said cantilevered tab to deflect.

5. The needle protector device recited in claim 4 wherein said mount has a second aperture disposed in said side of said mount and a second assembly slot extending from said lower end of said mount toward said upper end of said mount and wherein said cover has a second cantilevered tab disposed at an upper end of said cover and supporting a second lug for engaging said second assembly slot during assembly and said second aperture as said cover is moved between said needle protection position and said retracted position.

6. The needle protector device recited in claim 1 further comprising a spring coupled to said protective cover and extending through said mount.

7. The needle protector device recited in claim 1 wherein said mount is a unitary part.

8. The needle protector device recited in claim 1 wherein said mount has an assembly slot extending from said lower end of said mount toward said upper end of said mount through which said lug is directed during assembly.

9. A needle protector device comprising:
a needle having a tip;
a hub having an upper end adapted for coupling to a unit operative with said needle and a lower end to which said needle is attached;
a mount having an upper end coupled to said hub, an open lower end, and an aperture disposed in a side thereof;
a protective cover having a diameter smaller than the diameter of said mount, said protective cover having an upper end disposed inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture, wherein said aperture includes an entrance position adjacent to said lower end of said mount and an armed position radially spaced from said entrance position by an angled portion of said mount, wherein said device is armed by rotating said cover to move said lug from said entrance position of said aperture over said angled portion of said mount and to said armed position of said aperture; and
a spring couple to said cover for urging said cover from said retracted position to said needle protection position in which said lug is disposed in said entrance position of said aperture.

10. A needle protector device comprising:
a needle having a tip;
a hub having an upper end adapted for coupling to a unit operative with said needle and a lower end to which said needle is attached;
a mount having an upper end attached to said hub, an open lower end, and an aperture disposed in a side thereof; and
a protective cover having a diameter smaller than the diameter of said mount, said protective cover having an upper end fitting inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture, wherein said aperture includes an entrance position adjacent to said lower end of said mount and an armed position radially spaced from said entrance position by an angled portion of said mount, wherein said device is armed by rotating said cover to move said lug from said entrance position of said aperture to said armed position of said aperture, and wherein a spring is coupled between said mount and said cover, said spring providing a rotary force to move said lug radially in said aperture and an axial force to move said lug toward said lower end of said mount.

11. A needle protector device comprising:
a needle having a tip;
a hub having an upper end adapted for coupling to a unit operative with said needle and a lower end to which said needle is attached;
a mount having an upper end attached to said hub, an open lower end, and an aperture disposed in a side thereof; and
projective cover having a diameter smaller than the diameter of said mount, said protective cover having an upper end fitting inside of said lower end of said mount and an apertured lower end, wherein said cover is adapted for being in a needle protection position in which said lower end of said cover is disposed over said needle tip or a retracted position in which said needle tip extends through said apertured lower end of said cover, wherein said cover has a lug for engaging said aperture of said mount so that, as said cover is moved between said needle protection position and said retracted position, said lug moves within said aperture, wherein said aperture includes an entrance position adjacent to said lower end of said mount and an armed position radially spaced from said entrance position by an angled portion of said mount, wherein said device is armed by rotating said cover to move said lug from said entrance position of said aperture to said armed position of said aperture, and wherein said mount has an assembly slot extending from said lower end of said mount toward said upper end of said mount through which said lug is directed during assembly.

12. The needle protector device recited in claim 11 wherein said cover has a cantilevered tab disposed at said upper end of said cover and supporting said lug, said lug having a tapered edge which contacts said mount when said lug is moved from said assembly slot to said entrance position of said aperture during assembly causing said cantilevered tab to deflect.

13. The needle protector device recited in claim 9 wherein said mount is a unitary part.

14. The needle protector device recited in claim 9 wherein said mount has an assembly slot extending from said lower end of said mount toward said upper end of said mount through which said lug is directed during assembly.

15. A needle protector device comprising:
a needle;
a mount having an upper end at which a fitting and said needle are disposed said fitting being adapted for coupling to a unit operative with said needle, said mount further having an aperture disposed in a side thereof;
a protective cover having a diameter smaller than said mount, said protective cover having an upper end disposed in said lower end of said mount and an apertured lower end, wherein said cover is adapted for being in a protective position in which said lower end of said cover is disposed over said needle or a retracted position in which said needle is exposed through said apertured lower end of said cover, said cover having a lug for mating with said aperture so that said cover is moved between said protective position and said retracted position as said lug moves through said aperture; and
a spring, coupled between said mount and said cover and being responsive to axial and rotary biasing, for urging said lug to move in said aperture.

16. The needle protector device recited in claim 15 wherein said spring is coupled between said upper end of said mount and said upper end of said cover, said spring providing a rotary force to move said lug through said slot and an axial force to move said lug toward said lower end of said mount.

17. The needle protector device recited in claim 15 wherein said slot comprises an entrance slot extending from said lower end of said mount toward said upper end of said mount, an exit slot extending from said upper end of said mount toward said lower end of said mount, and a crossover slot extending between said entrance slot and said exit slot at ends of said entrance and exit slots distal from said lower end of said mount.

18. The needle protector device recited in claim 17 wherein said crossover slot extends from said ends of said entrance and exit slots distal from said lower end of said mount toward said upper end of said mount.

19. The needle protector device recited in claim 17 wherein said slot further comprises a ridge disposed at said lower end of said mount for receiving said lug to maintain said cover in said protective position.

20. The needle protector device recited in claim 17 wherein said slot further comprises an arming slot extending in an upward slope from said ridge to a lower end of said entrance slot.

21. The needle protector device recited in claim 15 wherein said mount is a unitary part.

22. A needle protector device comprising:
a mount having a hub at an upper end and an open lower end, said hub having a needle attached thereto and being adapted for coupling to a unit operative with said needle; and
a protective cover coupled to said mount and having an apertured lower end, wherein said cover is adapted for being in a needle protection position in which said lower end of said cover is disposed over said needle and said cover is prevented from being retracted to expose said needle, in an armed position in which said lower end of said cover is disposed over said needle and said cover is retractable to expose said needle, or in a retracted position in which said needle extends through said apertured lower end of said cover, wherein said cover is automatically moveable from said retracted position to said needle protection position.

23. The needle protector device recited in claim 22 wherein said mount has an aperture in a side thereof and said cover has a lug for engaging said aperture of said mount so that, as said cover is moved between said needle protection position, said armed position, and said retracted position, said lug moves in said aperture.

24. The needle protector device recited in claim 23 further comprising a spring coupled to said cover and extending through said mount, said spring providing a force to automatically move said cover from said retracted position to said needle protection position.

25. The needle protector device recited in claim 22 wherein said mount is a unitary part.

26. A needle protector device comprising:
a mount having a hub at an upper end and an open lower end, said hub having a needle attached thereto and being adapted for coupling to a unit operative with said needle;
a protective cover coupled to said mount and having an apertured lower end, wherein said cover is adapted for being in a needle protection position in which said lower end of said cover is disposed over said needle and said cover is prevented from being retracted to expose said needle, an armed position in which said lower end of said cover is disposed over said needle and said cover is prevented from moving to said needle protection position, and a retracted position in which said needle extends through said apertured lower end of said cover; and
a spring coupled to said cover for urging said cover from said retracted position to said needle protection position.

27. The needle protector device recited in claim 26 wherein said mount has an aperture disposed in a side thereof, said aperture having an entrance position and an armed position spaced from said entrance position by a portion of said mount protruding into said aperture, and wherein said cover has a lug in engagement with said aperture of said mount, whereby said protruding portion of said mount prevents said cover from moving to said needle protection position when said cover is in said armed position with said lug in the armed position of said aperture.

28. The needle protector device recited in claim 26 wherein said mount is a unitary part.

* * * * *

UNITED STATES PATENT AND TRADEMARK OFFICE
CERTIFICATE OF CORRECTION

PATENT NO. : 5,389,085
DATED : Feb. 14, 1995
INVENTOR(S) : Larry M. D'Alessio, et al.

It is certified that error appears in the above-indentified patent and that said Letters Patent is hereby corrected as shown below:

Column 7, line 33, "labelled "1"," should read --labelled "1",--.

Column 9, line 29, ""1" to permit" should read --"1" to permit--.

Column 10, line 20, "Upper" should read --upper---.

Column 12, line 38, "projective cover" should read --a protective cover--.

Column 13, line 11, "disposed said" should read --disposed, said--.

Signed and Sealed this

Nineteenth Day of September, 1995

Attest:

BRUCE LEHMAN

*Attesting Officer*    *Commissioner of Patents and Trademarks*